(12) United States Patent
Horie et al.

(10) Patent No.: US 10,138,266 B2
(45) Date of Patent: Nov. 27, 2018

(54) METHOD OF CUTTING OUT RNA OLIGONUCLEOTIDE

(71) Applicant: Nitto Denko Corporation, Ibaraki-shi, Osaka (JP)

(72) Inventors: Shohei Horie, Ibaraki (JP); Tatsuya Konishi, Ibaraki (JP); Kenjiro Mori, Ibaraki (JP); Eri Maeta, Ibaraki (JP); Tsuyoshi Mukobata, Ibaraki (JP); Masafumi Iwamoto, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/185,875

(22) Filed: Jun. 17, 2016

(65) Prior Publication Data

US 2017/0002038 A1    Jan. 5, 2017

(30) Foreign Application Priority Data

Jun. 18, 2015  (JP) ................................ 2015-123222

(51) Int. Cl.
| | |
|---|---|
| *C07H 21/00* | (2006.01) |
| *C07H 21/02* | (2006.01) |
| *C12Q 1/6806* | (2018.01) |
| *C12N 15/10* | (2006.01) |
| *C07H 1/06* | (2006.01) |

(52) U.S. Cl.
CPC .............. *C07H 21/02* (2013.01); *C07H 1/06* (2013.01); *C12N 15/1006* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 5,804,683 A | 9/1998 | Usman et al. | |
| 5,869,696 A | * 2/1999 | Reddy | .................... C07H 21/00 536/25.3 |
| 7,041,817 B2 | 5/2006 | Usman et al. | |
| 2004/0147735 A1 | 7/2004 | Laurent et al. | |

FOREIGN PATENT DOCUMENTS

| | | |
|---|---|---|
| EP | 2357188 A1 | 8/2011 |
| EP | 2620444 A1 | 7/2013 |
| WO | WO 2009/140125 A2 | 11/2009 |

OTHER PUBLICATIONS

Kumar, G. Dhawan, R. Chandra, K. C. Gupta; Polyamine-assisted rapid and clean cleavage of oligonucleotides from cis-diol bearing universal support. Nucleic Acids Res 2002; 30 (23): e130. doi: 10.1093/nar/gnf130.*
Pon, "Solid-Phase Supports for Oligonucleotide Synthesis," *Current Protocols in Nucleic Acid Chemistry*, Unit 3.1, pp. 3.1.1-3.1.28 (2000).
Kumar et al., "Rapid conditions for the cleavage of oligodeoxyribonucleotides from cis-diol-bearing universal polymer supports and their deprotection," *Nucleic Acids Research*, 27(10): e2 (1999).
Lyttle et al., "A new universal linker for solid phase DNA synthesis," *Nucleic Acids Research*, 24(14): 2793-2798 (1996).

* cited by examiner

*Primary Examiner* — Patrick T Lewis
(74) *Attorney, Agent, or Firm* — Leydig, Voit & Mayer, Ltd.

(57) ABSTRACT

The invention provides a cut-out method capable of suppressing production of a byproduct, wherein the object RNA oligonucleotide is not cleaved from a universal linker, which is produced in cutting out the object RNA oligonucleotide from the universal support, and capable of increasing the yield of the object RNA oligonucleotide. The RNA oligonucleotide cut-out method includes a step of bringing a universal support supporting an RNA oligonucleotide in contact with an aqueous solution containing alkylamine and a monovalent inorganic salt.

4 Claims, 2 Drawing Sheets

Specification includes a Sequence Listing.

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthesized Combined DNA/RNA
<220> FEATURE:
<221> NAME/KEY: misc_feature
<222> LOCATION: (21)..(21)
<223> OTHER INFORMATION: n = deoxythymidine

<400> SEQUENCE: 1
cgagaagcgc gauaccaugu n                                              21

<210> SEQ ID NO 2
<211> LENGTH: 19
<212> TYPE: RNA
<213> ORGANISM: Artificial Sequence
<220> FEATURE:
<223> OTHER INFORMATION: Synthesized RNA

<400> SEQUENCE: 2
ccauuaacga gcugcuuaa                                                 19

```
<210> SEQ ID NO 3
<211> LENGTH: 19
<212> TYPE: RNA
<213> ORGANISM: Artificial Sequence
<220> FEATURE:
<223> OTHER INFORMATION: Synthesized RNA

<400> SEQUENCE: 3
uuaagcagcu cguuaaugg                                              19
```

METHOD OF CUTTING OUT RNA OLIGONUCLEOTIDE

CROSS-REFERENCE TO RELATED APPLICATIONS

This patent application claims the benefit of Japanese Patent Application No. 2015-123222, filed on Jun. 18, 2015, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 890 bytes ASCII (Text) file named "725709SequenceListing.txt," created Jun. 16, 2016.

TECHNICAL FIELD OF THE INVENTION

The present invention generally relates to the field of chemical synthesis of a nucleic acid. More particularly, it relates to a method of cutting out RNA oligonucleotide from a solid phase carrier.

BACKGROUND OF THE INVENTION

A solid phase synthesis process using a phosphoramidite method has been widely used for the chemical synthesis of nucleic acids such as DNA oligonucleotide, RNA oligonucleotide and the like. In the solid phase phosphoramidite method, nucleic acid synthesis is generally performed by the following steps.

First, a nucleoside to be the 3'-terminus of a nucleic acid to be synthesized is ester bonded to a cleavable linker such as succinyl group and the like via a 3'-OH group to be previously supported on a carrier for solid phase synthesis (nucleoside linker). Then, the carrier for solid phase synthesis, on which the nucleoside linker is supported, is placed in a reaction column and set on a nucleic acid automatic synthesizer.

According to the synthesis program of a nucleic acid automatic synthesizer, a synthesis reaction including the following steps is generally performed in a reaction column:
(1) a step of removing 5'-OH group of protected nucleoside with an acid such as trichloroacetic acid/dichloromethane solution and the like;
(2) a step of coupling nucleoside phosphoramidite (nucleic acid monomer) with a deprotected 5'-OH group in the presence of an activator (tetrazole etc.);
(3) a step of capping an unreacted 5'-OH group with acetic anhydride and the like; and
(4) a step of oxidizing phosphite with aqueous iodine and the like. This synthesis cycle is repeated, and an elongation reaction of oligonucleotide is performed from the 3'-terminus to the 5'-terminus direction, whereby a nucleic acid having the object sequence is synthesized.

Lastly, a cleavable linker is hydrolyzed with aqueous ammonia, methylamine solution and the like, and the synthesized nucleic acid is cleaved from the carrier for solid phase synthesis (non-patent document 1). In addition, cleavage with an aqueous sodium hydroxide solution containing NaCl has also been reported (non-patent document 2).

When the above-mentioned synthesis is performed, as mentioned above, nucleoside as a starting material to be the 3'-terminus needs to be supported on a carrier for solid phase synthesis in advance via a cleavable linker. The 3'-terminus varies depending on the sequence of a nucleic acid desired to be synthesized, 4 kinds of dA, dG, dC, dT are necessary in the case of DNA oligonucleotide, and 4 kinds of rA, rG, rC, rU are necessary in the case of RNA oligonucleotide. When a modified oligonucleotide is to be synthesized, the process becomes complicated since a carrier for solid phase synthesis previously made to support a modified nucleoside is necessary.

To overcome the aforementioned problems, a carrier supporting a universal linker for solid phase synthesis (universal support) has been proposed as a linker connecting the solid phase carrier and the starting material, instead of a nucleoside-succinyl linker and the like generally used heretofore. When a universal support is used, irrespective of the kind of the nucleoside or nucleotide to be the 3'-terminus of a nucleic acid desired to be synthesized, synthesis is started by reacting nucleoside phosphoramidide to be the 3'-terminus by the same steps as those of general nucleic acid automatic synthesis, and after synthesis, the object nucleic acid is cut out from the universal support by a method similar to a conventional method. Advantageously, as mentioned above, a carrier supporting various nucleoside-linkers for solid phase synthesis is not required.

Conventionally, as a method of cutting out RNA oligonucleotide from a universal support, a method including contact with alkylamine or aqueous ammonia/alkylamine mixed solution has been generally used (patent document 1). In recent years, moreover, a method including contact with ethanolamine has been developed (patent document 4). In these methods, however, RNA oligonucleotide cannot be cleaved well from the universal linker, a large amount of byproduct is produced, and the object RNA oligonucleotide cannot be cut out with good purity. That is, in a method of cutting out the object RNA oligonucleotide from a universal support, the solid phase carrier alone is cleaved, RNA oligonucleotide cannot be cleaved well from the universal linker, and a byproduct is sometimes produced. While the bond between the RNA oligonucleotide and the universal linker can be cleaved by a stronger nucleophilic reagent, more harsh temperature conditions and the like, the cleavage particularly promotes decomposition of RNA oligonucleotide, which is considered to decrease the yield of the object RNA oligonucleotide. On the other hand, when cutting out is performed under mild conditions in an attempt to increase the yield of RNA oligonucleotide, byproducts wherein RNA oligonucleotide and universal linker are not cleaved may result in large amounts. In addition, since the byproduct and the object RNA oligonucleotide have similar properties such as molecular weight, polarity and the like, purification thereof by separation and purification techniques such as chromatography and the like is problematically difficult. Mainly for these reasons, use of a universal support is difficult in the synthesis of RNA oligonucleotide.

DOCUMENT LIST

Patent Documents

[patent document 1] U.S. Pat. No. 5,804,683 A
[patent document 2] US 20040147735 A1
[patent document 3] U.S. Pat. No. 7,041,817 B2
[patent document 4] WO 2009140125 A2

Non-Patent Documents

[non-patent document 1] Current Protocols in Nucleic Acid Chemistry (2000) 3.1.1-3.1.28
[non-patent document 2] Nucleic Acids Research (1999) Vol. 27, No. 10

SUMMARY OF THE INVENTION

Problems to be Solved by the Invention

The present invention aims to provide a cut-out method capable of suppressing production of a byproduct wherein RNA oligonucleotide is not cleaved from a universal linker, which is produced in cutting out the object RNA oligonucleotide from a universal support, and increasing the yield of the object RNA oligonucleotide.

Means of Solving the Problems

The present inventors have conducted intensive studies in an attempt to solve the aforementioned problems and found that production of a byproduct can be suppressed and the yield of the object RNA oligonucleotide can be increased by, in a method of cutting out the object RNA oligonucleotide from a universal support, bringing a solid phase oligonucleotide in contact with an aqueous solution containing alkylamine and a monovalent inorganic salt, which resulted in the completion of the present invention.

Accordingly, the present invention provides the following.

[1] A method of cutting out an RNA oligonucleotide chemically synthesized on a universal support from the support, comprising
   a step of bringing the support carrying the RNA oligonucleotide in contact with an aqueous solution containing alkylamine and a monovalent inorganic salt.
[2] The method described in the above-mentioned [1], wherein the aforementioned aqueous solution further comprises an alcohol.
[3] The method described in the above-mentioned [1] or [2], wherein the aforementioned alkylamine is primary alkylamine.
[4] The method described in any of the above-mentioned [1]-[3], wherein the concentration of the monovalent inorganic salt contained in the aforementioned aqueous solution is 1-100 mM.
[5] A production method of RNA oligonucleotide, comprising
   a step of chemically synthesizing RNA oligonucleotide on a universal support, and
   a step of cutting out the synthesized RNA oligonucleotide from the support by the method described in any of the above-mentioned [1]-[4].

Effect of the Invention

The RNA oligonucleotide cut-out method of the present invention can suppress production of a byproduct, wherein the object RNA oligonucleotide is not cleaved from a universal linker, and increase the yield of the object RNA oligonucleotide.

DESCRIPTION OF EMBODIMENTS

Figure 1:
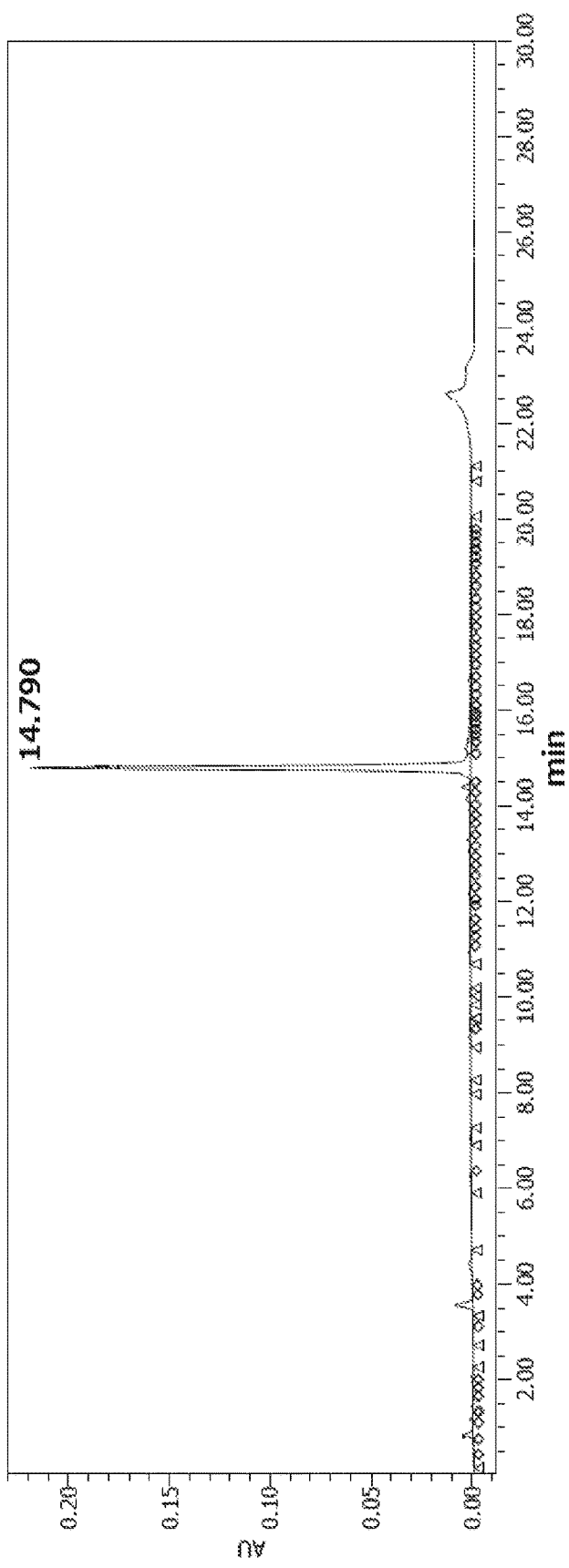
FIGS. 1 and 2 show the HPLC charts obtained in Example 1 and Comparative Example 1, respectively.

The present invention is explained in more detail by referring to preferable embodiments thereof.

The present invention provides a cut-out method of RNA oligonucleotide from a universal support. That is, a method of cutting out RNA oligonucleotide alone from a binding form of a universal linker and a chemically synthesized RNA oligonucleotide supported on a solid phase carrier. In a preferable embodiment of the method of the present invention, the phosphoric acid group on the 3'-terminus of RNA oligonucleotide can also be removed simultaneously with cutting out of the RNA oligonucleotide.

The reaction mechanism thereof is assumed to include the following process:
(a) a solid phase carrier is removed by cleavage of an ester bond between the solid phase carrier and a universal linker by alkylamine,
(b) as a result of (a), the negative electric charge produced on the oxygen of the universal linker forms a new PO bond with the phosphorus atom in the phosphoric acid group on the 3'-terminus of RNA oligonucleotide,
(c) almost simultaneously with (b), the PO bond between the phosphoric acid group on the 3'-terminus of the RNA oligonucleotide and sugar skeleton is cleaved, whereby the phosphoric acid group at the 3'-terminus of the RNA oligonucleotide and the universal linker are removed, to finally afford an RNA oligonucleotide wherein the phosphoric acid group on the 3'-terminus is removed.

In process (b), when the negative electric charge produced on the oxygen of the universal linker does not form a new PO bond with the phosphorus atom in the phosphoric acid group on the 3'-terminus of RNA oligonucleotide but instead forms an OH bond with the hydrogen atom (proton) present in the reaction system, a byproduct wherein the object RNA oligonucleotide is not cleaved from the universal linker is considered to be produced.

It is considered that a reaction resulting in a byproduct in process (b) can be efficiently suppressed by bringing a solid phase oligonucleotide in contact with an aqueous solution containing alkylamine and a monovalent inorganic salt, which characterizes the present invention. The aforementioned aqueous solution preferably contains alcohol.

According to the present invention, the object RNA oligonucleotide can be highly efficiently cut out, and drastic reduction of the production cost of RNA oligonucleotide can be achieved. Mass synthesis of RNA oligonucleotide by using a universal support, which could not be realized due to high costs heretofore, can also be achieved. That is, using one kind of universal support, a nucleic acid desired to be synthesized can be synthesized by reacting nucleoside phosphoramidide to be the 3'-terminus in the same steps as those of general nucleic acid automatic synthesis, irrespective of the kind of the nucleoside or nucleotide on the 3'-terminus of the nucleic acid desired to be synthesized. Furthermore, the object RNA oligonucleotide can be cut out with high purity, which is assumed to contribute to the improvement of the quality of a nucleic acid pharmaceutical product which is the main industrial use of the RNA oligonucleotide.

In the present specification, the "nucleic acid" means a chain compound (oligonucleotide) wherein nucleotides are linked by a phosphodiester bond, and includes DNA, RNA and the like. While the nucleic acid may be any of a single strand and a double strand, it is preferably a single strand since efficient synthesis can be performed using a nucleic acid synthesizer. In the present specification, the "nucleic acid" includes not only an oligonucleotide containing purine bases such as adenine (A), guanine (G) and the like and pyrimidine bases such as thymine (T), cytosine (C), uracil (U) and the like, but also a modified oligonucleotide containing other modified heterocycle-type bases.

In the present specification, the "RNA oligonucleotide" is the above-mentioned "nucleic acid" which has one or more ribonucleotide units in the chain. The RNA oligonucleotide may contain ribonucleotide in not less than 10%, not less than 20%, not less than 30%, not less than 40%, not less than 50%, not less than 60%, not less than 70%, not less than 80%, not less than 90%, not less than 95%, or all, of the nucleotide units in the chain.

While the nucleotide length of the RNA oligonucleotide is not particularly limited, it is preferably 2-200 nucleotides. When the nucleotide length is too long, the yield and purity of the obtained nucleic acid decrease.

In the present specification, the "linker" refers to a molecule that links two substances via a covalent bond, and links a solid phase carrier and a nucleic acid in the nucleic acid solid phase synthesis.

In the present specification, the "universal linker" is a linker with which nucleoside phosphoramidide to be the 3'-terminus can be reacted in the same steps as those of general nucleic acid automatic synthesis, irrespective of the kind of the nucleoside or nucleotide on the 3'-terminus of the nucleic acid desired to be synthesized. For this end, a universal linker generally has two adjacent carbon atoms; one of the carbon atoms has an —OH group to be the starting point of the nucleic acid synthesis, and the other carbon atom has a group (e.g., —OH group, —NH2 group, —SH group) that becomes a nucleophilic group upon removal of the protecting group. Specific examples of the universal linker usable in the present invention include, but are not limited to, those used in the below-mentioned Examples, those described in JP-A-2011-088843 and JP-A-2013-177371, UnyLinker (registered trade mark) (manufactured by Isis Pharmaceuticals) and the like.

The "universal support" in the present specification is a carrier for solid phase synthesis, which carries a universal linker.

The solid phase carrier is not particularly limited as long as it can easily remove by washing a reagent used in excess and, for example, porous synthetic polymer carriers such as glass porous carriers, polystyrene carriers, acrylamide carriers and the like, and the like can be used. The solid phase carrier preferably has a functional group contributing to the nucleic acid synthesis. The functional group "contributing to the nucleic acid synthesis" refers to one capable of being the starting point of the nucleic acid synthesis and permitting linker addition. Specific examples thereof include amino group, hydroxy group and the like. Examples of the specific solid phase carrier include those described in JP-A-2011-088843 and JP-A-2013-177371, and the like. In a preferable embodiment, low-swelling polystyrene particles commercially available as NittoPhase (registered trade mark) (manufactured by Nitto Denko Corporation) can be used.

In the present specification, the "alkylamine" is preferably primary alkylamine, more preferably, methylamine, ethylamine, propylamine, or butylamine, most preferably, methylamine.

In the present specification, the "monovalent inorganic salt" includes, for example, lithium chloride, potassium chloride, sodium chloride, sodium bromide, potassium iodide and the like. Both cation and anion constituting monovalent inorganic salts and having higher atomic weights tend to show a higher effect of the invention. In consideration of the effect, easy handleability and easy availability, sodium bromide is preferable.

The concentration of the monovalent inorganic salt contained in the aqueous solution is preferably 1-100 mM, more preferably 5-80 mM.

In the present specification, the "alcohol" is preferably methanol, ethanol, propanol (isopropanol) or butanol. The presence or absence of a branch is not particularly limited. In consideration of the effect, easy handleability and easy availability, isopropanol is most preferable.

The content of alcohol in the aqueous solution is preferably 1-80% by volume, more preferably 3-60% by volume.

In the present specification, the "contact" includes, for example, immersion, stirring immersion, passage of liquid, filtration and the like.

In the present specification, preferable temperature and time of contact of an aqueous solution containing alkylamine and a monovalent inorganic salt and oligonucleotide on a solid phase carrier are not particularly limited. When the contact temperature is 20° C.±5° C., the contact time is preferably 1-24 hr, and when the contact temperature is 40° C.±5° C., the contact time is preferably 0.25-6 hr.

The present invention also provides a production method of RNA oligonucleotide, which uses the aforementioned cut-out method of the present invention. The production method includes a step of chemically synthesizing RNA oligonucleotide on the aforementioned universal support (nucleic acid synthesis reaction), and a step of cutting out the synthesized RNA oligonucleotide from the support by the aforementioned cut-out method.

In the present specification, the "nucleic acid synthesis reaction" means an elongation reaction of nucleotides particularly constituting a nucleic acid. That is, nucleoside is sequentially bound to nucleoside, nucleotide or oligonucleotide bound on a solid phase carrier to give an elongated oligonucleotide. Examples of the nucleic acid synthesis reaction include H-phosphonate method, phosphoester method, solid phase phosphoramidite method and the like. Of these, solid phase phosphoramidite method is preferable since nucleic acid shows high synthesizability and highly pure nucleic acid can be obtained.

A preferable embodiment of the nucleic acid synthesis reaction by the solid phase phosphoramidite method includes a method containing each of the following steps:

(a) a step of placing a universal support in a reaction column of a nucleic acid automatic synthesizer;

(b) a step of flowing an acid such as a dichloroacetic acid solution and the like through a reaction column to remove a hydroxy-protecting group, washing same;

(c) a step of performing a series of steps of coupling nucleoside phosphoramidite corresponding to the 3'-terminus and activated by tetrazole and the like to the aforementioned hydroxy group, capping unreacted hydroxy group, and oxidation of phosphite, and repeating the series until the object sequence is obtained; and (d) a step of affording the object RNA oligonucleotide by subjecting, after completion of the synthesis steps with an apparatus, a carrier for nucleic acid solid phase synthesis to the aforementioned cut-out method of the present invention.

EXAMPLES

The present invention is explained in more detail in the following by referring to Examples, which are not to be construed as limitative.

[Experiment 1]

(Synthesis of RNA Oligonucleotide)

Universal supports (NittoPhase (registered trade mark) (manufactured by Nitto Denko Corporation)) bound with universal linkers of the following (A)-(D) in an amount corresponding to 1 μmol of the universal linker were each filled in a reaction column, and RNA oligonucleotide of 21 mer (5'r(CGAGAAGCGCGAUACCAUGU)dT3') (SEQ ID NO: 1) was synthesized using nucleic acid synthesizer nS-8II (manufactured by GeneDesign, Inc.).

(A) Universal support bound with UnyLinker (registered trade mark) (manufactured by Isis Pharmaceuticals) of the following Figure

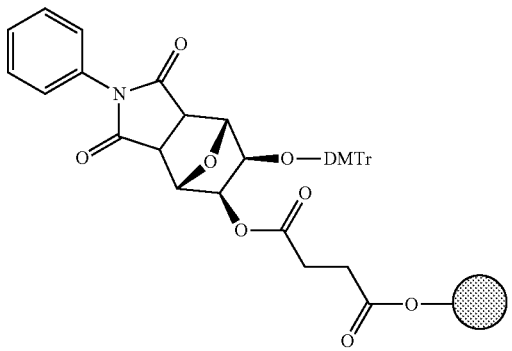

(B) Universal support of the following Figure

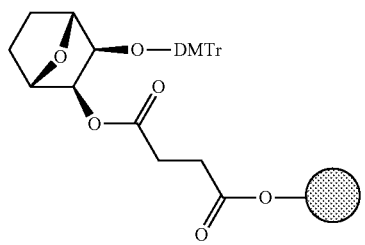

(C) Universal support of the following Figure

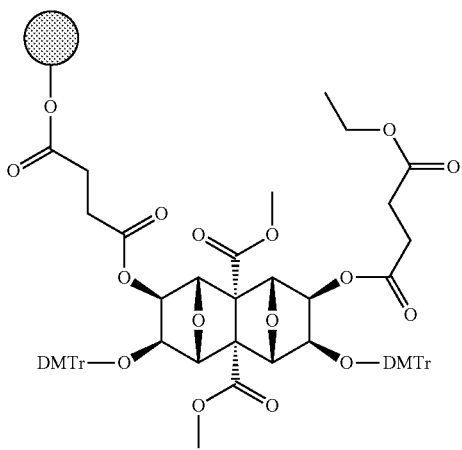

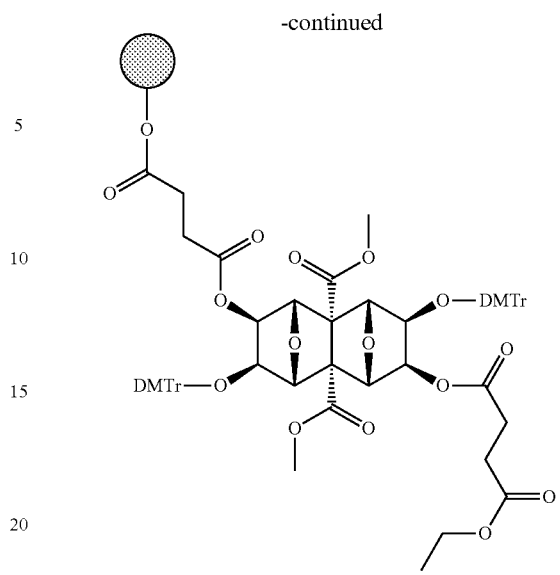

(D) Universal support of the following Figure

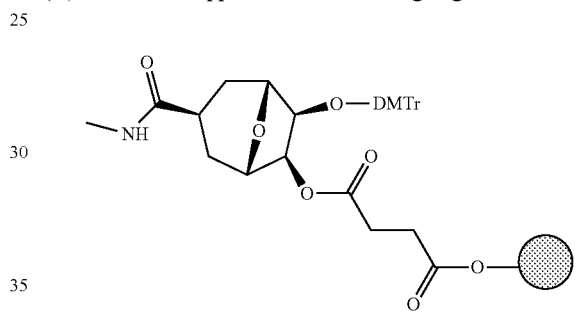

Example 1

After synthesis of RNA oligonucleotide by using the universal support of (A), a solid phase carrier bound with the RNA oligonucleotide was immersed in 20 mM sodium bromide-containing 40% aqueous methylamine solution/isopropanol (1:1) mixed solution at 45° C. for 4 hr, whereby the RNA oligonucleotide was cut out from the solid phase carrier. To this solution were added dimethyl sulfoxide and triethylamine hydrogen trifluoride in this order, and the mixture was heated at 45° C. for 1.5 hr to remove RNA 2'-terminus protecting group (tertiary butyldimethoxysilyl protecting group). To this solution was added 50 mM sodium acetate solution, and the mixture was diluted with water to give an RNA oligonucleotide sample solution.

Examples 2-4

In the same manner as in Example 1 except that the universal support of (A) was changed to the universal support of (B), an RNA oligonucleotide sample solution of Example 2 was obtained.

In the same manner as in Example 1 except that the universal support of (A) was changed to the universal support of (C), an RNA oligonucleotide sample solution of Example 3 was obtained.

In the same manner as in Example 1 except that the universal support of (A) was changed to the universal support of (D), an RNA oligonucleotide sample solution of Example 4 was obtained.

Comparative Example 1

After synthesis of RNA oligonucleotide by using the universal support of (A), a solid phase carrier bound with the RNA oligonucleotide was immersed in 28% aqueous ammonia/40% aqueous methylamine solution (1:1) mixed solution at 65° C. for 1.5 hr, whereby the RNA oligonucleotide was cut out from the solid phase carrier. To this solution were added dimethyl sulfoxide and triethylamine hydrogen trifluoride in this order, and the mixture was heated at 65° C. for 1.5 hr to remove RNA 2'-terminus protecting group (tertiary butyldimethoxysilyl protecting group). To this solution was added 50 mM sodium acetate solution, and the mixture was diluted with water to give an RNA oligonucleotide sample solution.

Comparative Examples 2-4

In the same manner as in Comparative Example 1 except that the universal support of (A) was changed to the universal support of (B), an RNA oligonucleotide sample solution of Comparative Example 2 was obtained.

In the same manner as in Comparative Example 1 except that the universal support of (A) was changed to the universal support of (C), an RNA oligonucleotide sample solution of Comparative Example 3 was obtained.

In the same manner as in Comparative Example 1 except that the universal support of (A) was changed to the universal support of (D), an RNA oligonucleotide sample solution of Comparative Example 4 was obtained.

(Measurement of RNA Oligonucleotide Purity and Amount of Byproduct)

The RNA oligonucleotide sample solutions obtained in Examples 1-4 and Comparative Examples 1-4 were measured for the absorbance (OD/μmol: OD per 1 μmol of universal linker) by an absorption spectrophotometer.

Figure 2:
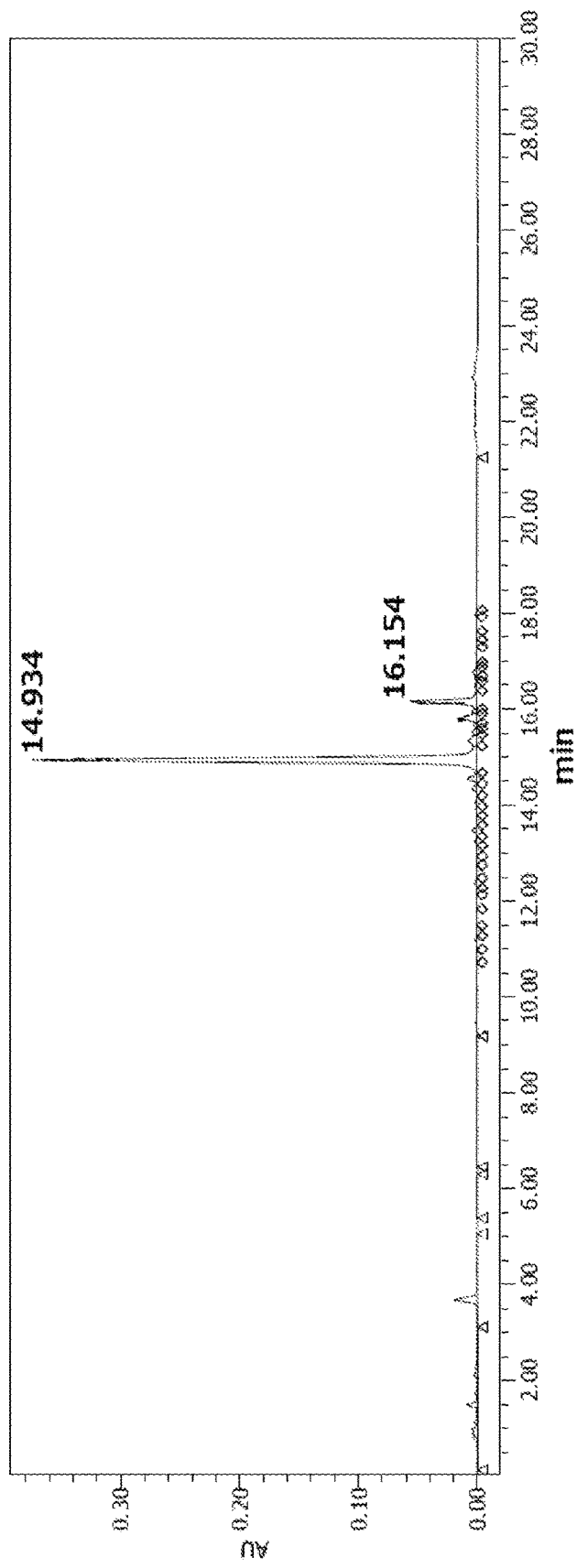

In addition, the RNA oligonucleotide sample solutions obtained in Examples 1-4 and Comparative Examples 1-4 were measured by high performance liquid chromatography (HPLC) (measurement condition: column; Waters XBridge OST C18 2.5 μm 50×4.6 mm, UV detection; 260 nm, Buffer A; 100 mM HFIP/7 mM TEA in water, pH 8.0, Buffer B; methanol, temperature; 60° C.). The HPLC charts obtained in Example 1 and Comparative Example 1 are shown in FIGS. 1 and 2, respectively. In FIGS. 1 and 2, the retention time of the object RNA oligonucleotide was around 14.8 min, and the retention time of a byproduct of a universal linker bound to RNA oligonucleotide was detected around 16.2 min.

Table 1 shows the data obtained in Experiment 1. In the Examples, it was confirmed that OD×FLP ((absorbance per 1 μmol of universal linker:OD:Optical Density)×(purity of the object RNA oligonucleotide calculated by HPLC measurement: FLP:Full Length Purity)), which is an index of the yield of RNA oligonucleotide, increased, and the production of a byproduct wherein a universal linker is bound to the object RNA oligonucleotide was suppressed. On the other hand, in Comparative Examples, it was confirmed that the purity of RNA oligonucleotide was lower than that in the Examples, and the amount of byproduct was high.

TABLE 1

| universal support | Example | | | | Comparative Example | | | |
|---|---|---|---|---|---|---|---|---|
| | OD/ umol | FLP (%) | OD × FLP | by-product (%) | OD/ umol | FLP (%) | OD × FLP | by-product (%) |
| (A) | 127 | 79 | 101 | 1 | 132 | 66 | 87 | 12 |
| (B) | 112 | 73 | 82 | 5 | 117 | 43 | 50 | 32 |
| (C) | 131 | 70 | 92 | 5 | 135 | 44 | 59 | 18 |
| (D) | 130 | 76 | 99 | 1 | 140 | 53 | 75 | 22 |

[Experiment 2]
(Synthesis of RNA Oligonucleotide)

The universal support of (A) in an amount corresponding to 151 μmol of the universal linker was filled in a reaction column, and RNA oligonucleotide of 21 mer (5'r(CGAGAAGCGCGAUACCAUGU)dT3') (SEQ ID NO: 1) was synthesized using nucleic acid synthesizer AKTA oligopilot plus 100 (manufactured by GE Healthcare Japan).

Examples 5-11

Aqueous solutions (cut out reagents) having the following composition were prepared.

Example 5: (E) 20 mM lithium chloride-containing 40% aqueous methylamine solution/isopropanol (1:1) mixed solution Example 6: (F) 20 mM potassium chloride-containing 40% aqueous methylamine solution/isopropanol (1:1) mixed solution Example 7: (G) 20 mM potassium iodide-containing 40% aqueous methylamine solution/isopropanol (1:1) mixed solution Example 8: (H) 20 mM sodium chloride-containing 40% aqueous methylamine solution/isopropanol (1:1) mixed solution Example 9: (I) 20 mM sodium bromide-containing 40% aqueous methylamine solution/isopropanol (1:1) mixed solution Example 10: (J) 20 mM sodium bromide-containing 40% aqueous methylamine solution/ethanol (1:1) mixed solution Example 11: (K) 20 mM sodium bromide-containing 40% aqueous methylamine solution A solid phase carrier, wherein the aforementioned RNA oligonucleotide was bound, was immersed in the above-mentioned cut out reagents (E)-(K) at 45° C. for 2 hr, whereby the RNA oligonucleotide was cut out from the solid phase carrier. To this solution were added dimethyl sulfoxide and triethylamine hydrogen trifluoride in this order, and the mixture was heated at 60° C. for 1 hr to remove RNA 2'-terminus protecting group (tertiary butyldimethoxysilyl protecting group). To this solution was added 50 mM sodium acetate solution, and the mixture was diluted with water to give an RNA oligonucleotide sample solution.

Comparative Examples 5-7

In the same manner as in Example 5 except that aqueous solutions (cut out reagents) having the following composition were prepared, RNA oligonucleotide sample solutions were obtained.

Comparative Example 5: (L) 40% aqueous methylamine solution

Comparative Example 6: (M) 40% aqueous methylamine solution/28% aqueous ammonia (1:1) mixed solution Comparative Example 7: (N) 40% aqueous methylamine solution/isopropanol (1:1) mixed solution (Measurement of RNA Oligonucleotide Yield and Amount of Byproduct)

The RNA oligonucleotide sample solutions obtained in Examples 5-11 and Comparative Examples 5-7 were measured by high performance liquid chromatography (HPLC) under conditions similar to those of Examples 1-4 and Comparative Examples 1-4.

Table 2 shows the data obtained in Experiment 2. In the Examples, it was confirmed that peak area/nmol (HPLC peak area of RNA oligonucleotide per 1 nmol of universal linker), which is an index of the yield of RNA oligonucleotide, increased, and the production of a byproduct wherein a universal linker is bound to the object RNA oligonucleotide was suppressed.

TABLE 2

| kind of cut out reagents | | kind of monovalent inorganic salt | kind of alcohol | peak area/nmol | FLP (%) | byproduct (%) |
|---|---|---|---|---|---|---|
| Example 5 | (E) | LiCl | isopropanol | 4380000 | 63 | 2 |
| Example 6 | (F) | KCl | isopropanol | 4460000 | 63 | 2 |
| Example 7 | (G) | KI | isopropanol | 4020000 | 62 | 2 |
| Example 8 | (H) | NaCl | isopropanol | 4370000 | 64 | 1 |
| Example 9 | (I) | NaBr | isopropanol | 4830000 | 66 | 1 |
| Example 10 | (J) | NaBr | ethanol | 4590000 | 65 | 1 |
| Example 11 | (K) | NaBr | — | 2700000 | 49 | 2 |
| Comparative Example 5 | (L) | — | — | 1810000 | 29 | 7 |
| Comparative Example 6 | (M) | — | (28% aqueous ammonia) | 2570000 | 46 | 14 |
| Comparative Example 7 | (N) | — | isopropanol | 3990000 | 53 | 10 |

[Experiment 3]

Aqueous solutions (cut out reagents) having the following composition were prepared.

Example 12: (O) 10 mM sodium bromide containing 40% aqueous methylamine solution/isopropanol (1:1) mixed solution Example 13: (P) 20 mM sodium bromide containing 40% aqueous methylamine solution/isopropanol (1:1) mixed solution Example 14: (Q) 30 mM sodium bromide-containing 40% aqueous methylamine solution/isopropanol (1:1) mixed solution Example 15: (R) 20 mM sodium bromide-containing 40% aqueous methylamine solution/isopropanol (9:1) mixed solution Example 16: (S) 20 mM sodium bromide-containing 40% aqueous methylamine solution/isopropanol (8:2) mixed solution Example 17: (T) 20 mM sodium bromide-containing 40% aqueous methylamine solution/isopropanol (6:4) mixed solution Example 18: (U) 60 mM sodium bromide-containing 40% aqueous methylamine solution/isopropanol (95:5) mixed solution Example 19: (V) 60 mM sodium bromide-containing 40% aqueous methylamine solution/isopropanol (9:1) mixed solution Example 20: (W) 60 mM sodium bromide-containing 40% aqueous methylamine solution/isopropanol (8:2) mixed solution The solid phase carrier obtained in Experiment 2, wherein the RNA oligonucleotide was bound, was immersed in the cut out reagents of Examples 12-17 ((O)-(T)) at 45° C. for 2 hr and immersed in the cut out reagents of Examples 18-20 ((U)-(W)) at 23° C. for 4 hr, whereby the RNA oligonucleotide was cut out from the solid phase carrier. To this solution were added dimethyl sulfoxide and triethylamine hydrogen trifluoride in this order, and Examples 12-14 ((O)-(Q)) were heated at 60° C. for 1 hr, and Examples 15-20 ((R)-(W)) were heated at 45° C. for 1.5 hr to remove RNA 2'-terminus protecting group and TBDMS protecting group. To these solutions was added 50 mM sodium acetate solution, and the mixtures were diluted with water to give RNA oligonucleotide sample solutions.

(Measurement of RNA Oligonucleotide Yield and Amount of Byproduct)

Measurement was performed in the same manner as in Examples 5-11 and Comparative Examples 5-7.

Table 3 shows the data obtained in Experiment 3. In the Examples, it was confirmed that peak area/nmol (HPLC peak area of RNA oligonucleotide per 1 nmol of universal linker), which is an index of the yield of RNA oligonucleotide, increased, and the production of a byproduct wherein a universal linker is bound to the object RNA oligonucleotide was suppressed.

TABLE 3

| kind of cut out reagents | | amount of NaBr added (mM) | isopropanol ratio (%) | peak area/nmol | FLP (%) | byproduct (%) |
|---|---|---|---|---|---|---|
| Example 12 | (O) | 10 | 50 | 4480000 | 64 | 2 |
| Example 13 | (P) | 20 | 50 | 4980000 | 65 | <1 |
| Example 14 | (Q) | 30 | 50 | 4520000 | 63 | <1 |
| Example 15 | (R) | 20 | 10 | 4150000 | 61 | 1 |
| Example 16 | (S) | 20 | 20 | 4360000 | 62 | 1 |
| Example 17 | (T) | 20 | 40 | 4440000 | 66 | 1 |
| Example 18 | (U) | 60 | 5 | 2710000 | 57 | <1 |
| Example 19 | (V) | 60 | 10 | 3380000 | 58 | <1 |

TABLE 3-continued

| kind of cut out reagents | | amount of NaBr added (mM) | isopropanol ratio (%) | peak area/nmol | FLP (%) | byproduct (%) |
|---|---|---|---|---|---|---|
| Example 20 | (W) | 60 | 20 | 4070000 | 60 | <1 |
| Comparative Example 5 | (L) | — | — | 1810000 | 29 | 7 |
| Comparative Example 6 | (N) | — | 50 | 3990000 | 53 | 10 |

[Experiment 4]
(Synthesis of RNA Oligonucleotide)

The universal support of (A) in an amount corresponding to 80 µmol of the universal linker was filled in a reaction column, and RNA oligonucleotide of 19 mer (5'-r(CCAUUAACGAGCUGCUUAA)-3' (SEQ ID NO: 2) was synthesized using nucleic acid synthesizer AKTA oligopilot plus 100 (manufactured by GE Healthcare Japan).

Similarly, the universal support of (A) in an amount corresponding to 80 µmol of the universal linker was filled in a reaction column, and RNA oligonucleotide of 19 mer (5'-r(UUAAGCAGCUCGUUAAUGG)-3' (SEQ ID NO: 3) was synthesized using nucleic acid synthesizer AKTA oligopilot plus 100 (manufactured by GE Healthcare Japan).
(Cutting Out of RNA Oligonucleotide from Solid Phase Carrier)

An aqueous solution (cut out reagent) having the following composition was prepared.

cut out reagent (X): 80 M sodium bromide-containing 40% aqueous methylamine solution/isopropanol (8:2) mixed solution In Example 21, a solid phase carrier obtained as mentioned above, wherein RNA oligonucleotide of SEQ ID NO: 2 was bound, was immersed in cut out reagent (X) at 25° C. for 18 hr, whereby the RNA oligonucleotide was cut out from the solid phase carrier. In Example 22, a solid phase carrier obtained as mentioned above, wherein RNA oligonucleotide of SEQ ID NO: 3 was bound, was immersed in cut out reagent (X) at 25° C. for 14 hr, whereby the RNA oligonucleotide was cut out from the solid phase carrier.

To these solutions were added dimethyl sulfoxide and triethylamine hydrogen trifluoride in this order, and the mixture was heated at 65° C. for 1.5 hr to remove RNA 2'-terminus protecting group and TBDMS protecting group. To these solutions was added 50 mM sodium acetate solution, and the mixture was diluted with water to give an RNA oligonucleotide sample solution.
(Measurement of RNA Oligonucleotide Yield and Amount of Byproduct)

Measurement was performed in the same manner as in Examples 5-11 and Comparative Examples 5-7.

Table 4 shows the data obtained in Experiment 4. In Examples 21 and 22, it was confirmed that peak area/nmol (HPLC peak area of RNA oligonucleotide per 1 nmol of universal linker), which is an index of the yield of RNA oligonucleotide, increased, and the production of a byproduct wherein a universal linker is bound to the object RNA oligonucleotide was suppressed.

TABLE 4

| | peak area/nmol | FLP (%) | byproduct (%) |
|---|---|---|---|
| Example 21 | 4810643 | 71.2 | 2 |
| Example 22 | 5128200 | 75.9 | 3 |

The invention claimed is:

1. A method of cutting out an RNA oligonucleotide chemically synthesized on a universal support from the support, comprising
    a step of bringing the support carrying the RNA oligonucleotide in contact with an aqueous solution containing alkylamine and 10-60 mM monovalent inorganic salt.

2. The method according to claim 1, wherein said aqueous solution further comprises an alcohol.

3. The method according to claim 1, wherein said alkylamine is primary alkylamine.

4. A production method of RNA oligonucleotide, comprising
    a step of chemically synthesizing RNA oligonucleotide on a universal support, and
    a step of cutting out the synthesized RNA oligonucleotide from the support by the method according to claim 1.

* * * * *